United States Patent [19]
Just et al.

[11] 4,385,175
[45] May 24, 1983

[54] ESTERS OF RETINOIC ACID AND AZETIDINONE DERIVATIVES

[75] Inventors: George Just, Westmount; Gholam H. Hakimelahi, Montreal, both of Canada

[73] Assignee: Bristol-Myers Company, New York, N.Y.

[21] Appl. No.: 360,557

[22] Filed: Mar. 22, 1982

[51] Int. Cl.$^3$ ................. C07D 491/052; C07D 205/08
[52] U.S. Cl. .................................................... 542/426
[58] Field of Search ......................................... 542/426

[56] References Cited

U.S. PATENT DOCUMENTS 2,576,103  11/1951  Cawley et al. ...................... 568/824
4,216,224  8/1980  Yu et al. ............................. 424/286

OTHER PUBLICATIONS

Just et al., Can. J. of Chem., vol. 56(21), (1978), pp. 2720–2724, 2725–2730.
Just et al., Synthetic Comm., vol. 9(2), (1979), pp. 117–121.

Primary Examiner—Henry R. Jiles
Assistant Examiner—Bernard Dentz
Attorney, Agent, or Firm—Roylance, Abrams, Berdo & Farley

[57] ABSTRACT

There are disclosed esters of retinoic acid and alcohols which are azetidinone derivatives. These esters are useful as anti-cancer agents.

4 Claims, No Drawings

ESTERS OF RETINOIC ACID AND AZETIDINONE DERIVATIVES

BACKGROUND OF THE INVENTION

This invention relates to esters of retinoic acid and alcohols which are azetidinone derivatives. Such esters are useful as anti-cancer agents.

Retinoic acid, also known as Vitamin A acid, is a well known compound having the formula:

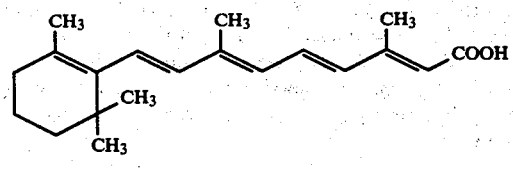

Various simple esters of retinoic acid are also known in the art as shown in U.S. Pat. Nos. 2,576,103 and 4,216,224.

Azetidinones have been described in the literature, Just et al (I), Can. J. Chem., 56, pp. 2720–2724 (1978); Just et al (II), Can. J. Chem., 56, pp. 2725–2730 (1978); and Just et al (III), Synth. Comm., 9, pp. 117–121 (1979). Just et al (I) disclose the preparation of compounds having the formula:

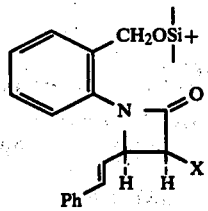

I

In Formula I and hereinafter, X is —$N_3$ or —NHCOCH$_2$Ph and Ph is phenyl. The compounds of Formula I may be hydrolyzed to form azetidinone alcohols having the formula:

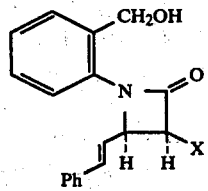

II

Just et al (II) disclose the preparation of a compound having the formula:

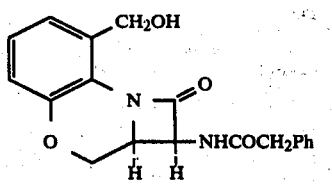

III

SUMMARY OF THE INVENTION

In accordance with this invention, there are provided retinoic acid esters of the alcohols of Formula II. Such esters have the formulas:

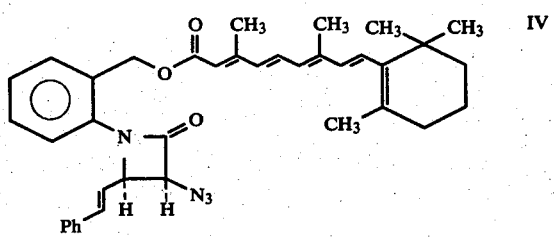

IV and

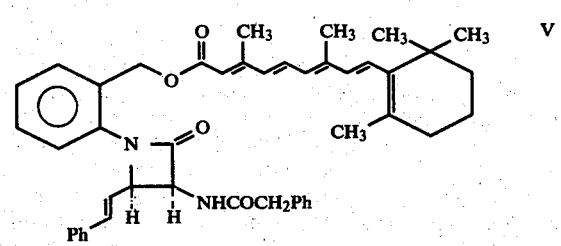

V

There is also provided the retinoic acid ester of the azetidinone alcohol of Formula III. This ester has the formula:

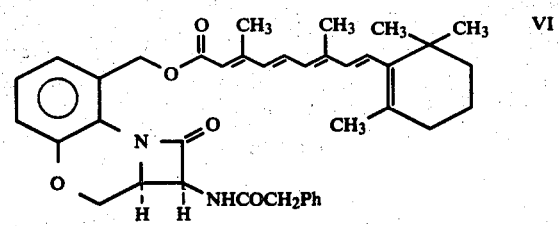

VI

In accordance with another aspect of this invention, there is provided the retinoic acid ester having the formula:

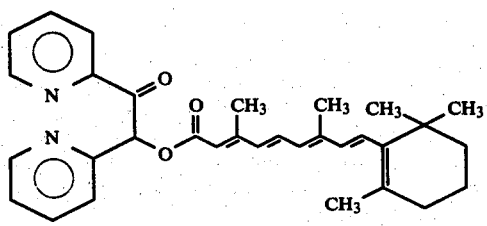

VII

DETAILED DESCRIPTION OF THE INVENTION

Just et al (III) describe the reaction of a wide range of substituted anilines with a pKa of approximately 2 or higher with cinnamaldehyde to provide a Schiff base. Treatment of the Schiff base with azidoacetyl chloride provides cis-β-lactams exclusively.

As shown in Just et al (I), the compound of Formula I wherein X is —$N_3$ is obtained as azide 18 (page 2723) which is reduced with hydrogen sulfide/triethylamine to the corresponding amine which is acylated with phenylacetyl chloride to yield amide 19 (page 2723).

Treatment of the azide 18 of Just et al (I) with fluoride ion gives the alcohol of Formula III wherein X is —$N_3$; and treatment of the amide 19 of Just et al (I) with fluoride ion gives the alcohol of Formula II wherein X is —$NHCOCH_2Ph$.

As shown in Just et al (II), the alcohol of Formula III is obtained by reaction of azide 26 (page 2728) with ozone, followed by sodium borohydride reduction to provide alcohol 27 (page 2728), which upon mesylation gives mesylate 28 (page 2729); mesylate 28 is cyclized to give azide 29a which is reduced with hydrogen sulfide/triethylamine to the corresponding amine which is acylated with phenacetyl chloride to yield amide 29b (page 2729); and amide 29b is treated with trifluoroacetic acid to give the alcohol amide 31 (page 2729).

The following examples are illustrative of the herein claimed invention:

EXAMPLE 1

The compound of Formula III, i.e., alcohol amide 31 of Just et al (II), was transformed to its mesylate as described in Just et al (II) for the conversion of alcohol 27 to mesylate 28 (pages 2728 and 2729). To the mesylate (1 mmol) in 3 ml of dimethyl formamide under a nitrogen atmosphere was added retinoic acid (1 mmol) and potassium carbonate (3 mmol) at room temperature. After 15 hours, ether was added, and the solution washed with water, dried over $MgSO_4$ and evaporated. Crystallization from pentane gave the desired ester having the structure of Formula VI, mp 85°–88° C.; $\lambda_{max}^{EtOH}$ 350 nm ($\epsilon$ 2010); ir $\nu^{CH_2Cl_2}$ 3400, 1770 ($\beta$-lactam), 1705 (ester), 1685 cm$^{-1}$ (amide); m/e (C.I.) 621 (M$^+$+H), nmr 1.02 (s, 6H, 2 $CH_3$), 1.2–2.4 (m, 15H, 3 $CH_3$, 3 $CH_2$), 3.51 (s, 2H, $CH_2$—O), 3.79–4.51 (m, 4H, $OCH_2CHCH$), 5.31 (s, 2H, $OCH_2Ph$), 5.61–6.71 (m, 7H, =CH and NH), 6.81–7.3 (m, 8H, Ph).

EXAMPLE 2

Step A

The compound of Formula I wherein X is —$N_3$, i.e., azide 18 of Just et al (I) (page 2723) is converted to the alcohol of Formula II wherein X is —$N_3$ by the same procedure described in Just et al (I) for the conversion of amide 22 to alcohol 23 (page 2724); i.r. 3500–3300 (OH), 2100 ($N_3$), 1761 ($\beta$-lactam) cm$^{-1}$.

Step B

The alcohol obtained in Step A was dissolved in methylene chloride. To this solution was added one equivalent of methanesulfonyl chloride and one equivalent of triethylamine at 0° C. The solution was washed with water, dried (MgSO$_4$) and evaporated to give the mesylate (a compound as defined in Formula I wherein X is —$N_3$ and the group

is replaced with the group $OSO_2CH_3$); i.r., 2100 ($N_3$), 1770 ($\beta$-lactam) cm$^{-1}$; n.m.r. $\delta$ (ppm), 2.95 (s, 3H, $SO_2CH_3$), 5.11 (m, 2H, $\beta$-lactam CH—CH), 5.4 (d, 2H, $CH_2O$), 6.01–6.98 (m, 2H, CH=CH), 7.39 (m, 9H, aromatic). This mesylate (1 mmol) was stirred in dimethyl formamide (DMF) (3 ml) containing retinoic acid (1 mmol) and $K_2CO_3$ (3 mmol) at room temperature for 15 hours. Dilution with water and three extractions with ether, followed by washing with water (3 x) gave, after purification over a charcoal column using diethyl ether as eluent, the retinoate of Formula IV in 90% yield; n.m.r. (CDCl$_3$) 1.09 (s, 6H, C(CH$_3$)$_2$), 1.22–2.45 (m, 15H, 3 $CH_3$,3 $CH_2$), 5.00–4.39 (m, 4H, $CH_2$ and $\beta$-lactam CH), 5.80–7.01 (m, 8H, =CH), 7.41 (m, 9H, Ph); i.r. (CH$_2$Cl$_2$) 1765 ($\beta$-lactam), 2100 (N$_3$), 1710 (ester); u.v. $\lambda_{max}$ (EtOH) 355 nm (1895); C.I. 603 (M+H).

EXAMPLE 3

Step A

The compound of Formula I wherein X is —NHCOCH$_2$Ph, i.e., azide 19 of Just et al (I) (page 2723) is converted to the alcohol of Formula II wherein X is —NHCOCH$_2$Ph by the same procedure described in Just et al (I) for the conversion of amide 22 to alcohol 23 (page 2724); i.r. 3480 (OH), 1734 ($\beta$-lactam), 1659 (amide) cm$^{-1}$.

Step B

The alcohol obtained in Step A was dissolved in methylene chloride. To this solution was added one equivalent of methanesulfonyl chloride and one equivalent of triethylamine at 0° C. The solution was washed with water, dried (MgSO$_4$) and evaporated to give the mesylate (a compound as defined in Formula I wherein X is —NHCOCH$_2$Ph and the group

is replaced with the group OSO$_2$CH$_3$); n.m.r. (CDCl$_3$)$\delta$ 2.99 (s, 3H, CH$_3$), 3.60 (s, 2H, CH$_2$Ph), 5.1 (bs, 2H, CH$_2$OMs), 5.31 (m, 1H, CH $\beta$-lactam), 5.4–5.8 (dd, 1H, CHN, J$_1$=5 Hz, J$_2$=10 Hz), 5.9–6.9 (m, 3H, NH and CH=CH), 7.2–7.4 (m, 14H, Ph); i.r. (CH$_2$Cl$_2$) 3400 (NH), 1770 ($\beta$-lactam), 1680 (amide) cm$^{-1}$. This mesylate was treated with one equivalent of retionic acid (1 mmol) in 3 ml DMF in the presence of three equivalents of K$_2$CO$_3$ which gave, after 15 hours, the retinoate of Formula V which was purified by a short column of charcoal, using ether as eluent; n.m.r. (CDCl$_3$), 1.01 (S, 6H, C(CH$_3$)$_2$), 1.41–2.41 (m, 15H, 3 CH$_3$ and 3 CH$_2$), 3.59 (s, 2H, CH$_2$CO), 4.51–5.05 (m, 4H, CH$_2$O and CHCH), 5.8–6.1 (m, 2H, =CH, NH), 7.2–7.4 (m, 14H, Ph); i.r. (CH$_2$Cl$_2$), 3400 (NH), 1760 ($\beta$-lactam), 1710 (ester) cm$^{-1}$; u.v. $\lambda_{max}$ (EtOH), 351 nm (1879); C.I. 695 (M$^+$+1).

EXAMPLE 4

The retinoate of Formula VII was prepared according to the following reaction sequence:

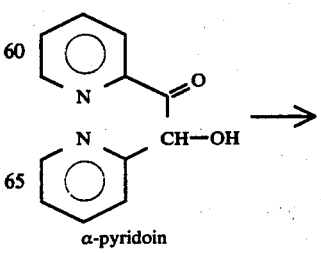

$\alpha$-pyridoin

-continued

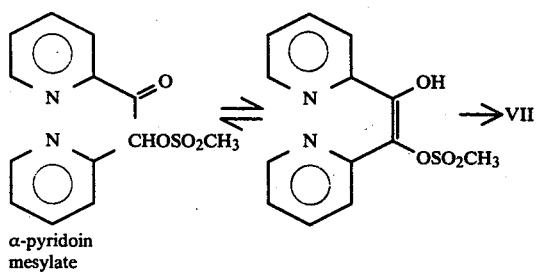

α-pyridoin mesylate

α-Pyridoin (2.14 g, 0.01 mol) was dissolved in 20 ml of methylene chloride and triethylamine (1.01 g, 0.01 mol) was added. Then, methanesulfonyl chloride (1.15 g, 0.01 mol) in 9 ml CH$_2$Cl$_2$ was added dropwise at 0° C. After 30 minutes, water was added and the organic layer was washed two times with water, dried, evaporated and purified on silica gel to give a quantitative yield of the mesyl derivative after elution with CHCl$_3$; n.m.r. (CDCl$_3$) δ3.00 (s, 3H, CH$_3$), 6.9–8.4 (m, 9H, pyridinic hydrogen and OH). The pyridoin mesylate (1 mmol) was dissolved in DMF (3 ml), and two equivalents of potassium carbonate, followed by 1 mmol of retinoic acid, were added. The solution was stirred under nitrogen for 15 hours at room temperature. Ether was added and the ethereal layer was washed with water (5 times), dried and evaported to give a quantitative yield of the retinoate of Formula VII, which was crystallized from pentane, m.p. 65°–67° C.; n.m.r. (CDCl$_3$) δ1.01 (s, 6H, C(CH$_3$), 1.40–2.41 (m, 15H, 3 CH$_3$ and 3 CH$_2$), 5.8–6.95 (m, 6H, =CH), 7.00–8.81 (m, 9H, aromatic pyridine and OH); i.r. (CH$_2$Cl$_2$), 3500 (OH), 1710 (ester), u.v. λ$_{max}$ (EtOH), 355 nm (2212); C.I. 497 (M$^+$+1).

The compounds of this invention are useful as anticancer agents—e.g., they exhibit antileukemia activity in laboratory animals.

The biological activities of the retinoic acid esters of this invention were evaluated according to their ability to inhibit squamous metoplasia and keratinization in organ cultures of trachea derived from vitamin A-deficient hamsters according to a procedure described by Sporn et al, Nature, 263, pages 110–113 (1976). The results are set forth in the following table.

TABLE

| Retinoid | Reversal of Keratinization ED$_{50}$[a] |
| --- | --- |
| β-All-trans-retinoic acid | 1.15 × 10$^{-10}$ M |
| Compound IV | 4.07 × 10$^{-10}$ M |
| Compound V | 1.98 × 10$^{-10}$ M |
| Compound VI | 3.90 × 10$^{-10}$ M |
| Compound VII | 3.10 × 10$^{-10}$ M |

[a]Median effective dose (ED$_{50}$) for reversal of keratinization is the dose required for reversal of keratinization of 50% of the explants as determined by probit analysis.

We claim:
1. The retinoic acid ester having the formula:

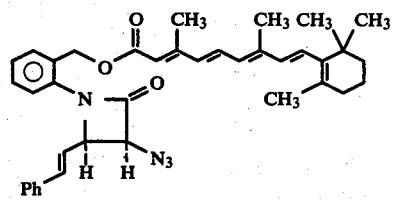

2. The retinoic acid ester having the formula:

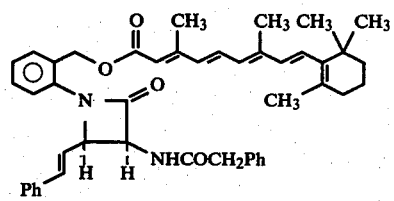

3. The retinoic acid ester having the formula:

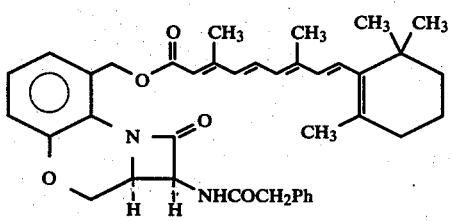

4. The retinoic acid ester having the formula:

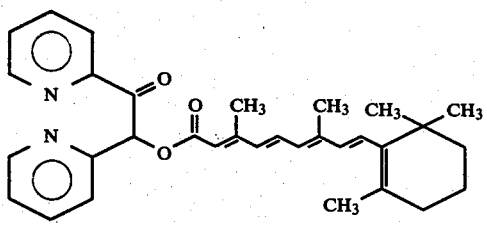

* * * * *